US012797213B2

(12) United States Patent
Curran et al.

(10) Patent No.: US 12,797,213 B2
(45) Date of Patent: Nov. 17, 2026

(54) DEVICES, SYSTEMS, AND METHODS FOR ENGAGEABLE STENTS

(71) Applicant: BOSTON SCIENTIFIC SCIMED, INC., Maple Grove, MN (US)

(72) Inventors: Darren Gerard Curran, Galway (IE); Gerard Duignan, Galway (IE); Paul E. Tierney, Galway (IE); David Collins, Galway (IE); John O'Driscoll, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 791 days.

(21) Appl. No.: 18/106,822

(22) Filed: Feb. 7, 2023

(65) Prior Publication Data

US 2023/0248553 A1 Aug. 10, 2023

Related U.S. Application Data

(60) Provisional application No. 63/307,775, filed on Feb. 8, 2022.

(51) Int. Cl.
*A61F 2/90* (2013.01)
*A61F 2/00* (2006.01)
(Continued)

(52) U.S. Cl.
CPC .......... *A61F 2/90* (2013.01); *A61F 2002/826* (2013.01); *A61F 2230/0069* (2013.01); (Continued)

(58) Field of Classification Search
None
See application file for complete search history.

(56) References Cited

U.S. PATENT DOCUMENTS 5,330,500 A * 7/1994 Song .......................... A61F 2/90 606/198
5,645,559 A * 7/1997 Hachtman ................ D04C 3/48 606/198

(Continued)

FOREIGN PATENT DOCUMENTS

JP 2014534844 A 12/2014
JP 2017170238 A 9/2017
JP 2020529884 A 10/2020

OTHER PUBLICATIONS

International Search Report and Written Opinion dated May 26, 2023 for International Application No. PCT/US2023/012513.

*Primary Examiner* — Ann Hu
(74) *Attorney, Agent, or Firm* — Seager, Tufte & Wickhem, LLP

(57) ABSTRACT

Engageable stents disclosed herein may include an outer stent comprising an elongate body configured to be expandable between a constrained configuration and an unconstrained configuration. The elongate body in the unconstrained configuration may include a retention member and a cylindrical saddle region adjacent the retention member, the cylindrical saddle region defining a lumen extending along a longitudinal axis of the outer stent. The retention member of the outer stent may comprise a double-walled flange. The engageable stents may include an inner stent comprising an elongate body configured to be expandable between a constrained configuration and an unconstrained configuration. The elongate body in the unconstrained configuration may include a retention member and a cylindrical saddle region adjacent the retention member. The retention member of the inner stent may comprise a double-walled flange. The retention members of the outer and inner stent may be removably engageable with each other.

14 Claims, 6 Drawing Sheets

(51) Int. Cl.
*A61F 2/04* (2013.01)
*A61F 2/852* (2013.01)
*A61F 2/82* (2013.01)

(52) U.S. Cl.
CPC . *A61F 2230/0095* (2013.01); *A61F 2250/001* (2013.01); *A61F 2250/0098* (2013.01)

(56) References Cited

U.S. PATENT DOCUMENTS 5,693,085 A * 12/1997 Buirge .................. A61F 2/91 623/1.13
5,723,003 A * 3/1998 Winston .................. A61F 2/954 623/1.13
5,725,552 A * 3/1998 Kotula .................. A61B 17/12022 604/509
6,139,573 A * 10/2000 Sogard .................. A61F 2/07 623/1.13
6,165,211 A * 12/2000 Thompson .................. B29C 55/22 623/1.13
6,245,100 B1 * 6/2001 Davila .................. A61F 2/91 606/198
7,060,089 B2 * 6/2006 Ley .................. A61F 2/91 623/1.15
7,591,845 B2 * 9/2009 Rhim .................. A61F 2/90 623/1.19
8,784,473 B2 * 7/2014 Tupil .................. A61F 2/07 623/1.33
9,839,511 B2 * 12/2017 Ma .................. A61F 2/2409
10,245,371 B2 * 4/2019 Cully .................. A61F 2/064
10,368,985 B2 * 8/2019 Wilson .................. A61F 2/844
10,722,341 B2 * 7/2020 Binmoeller .................. A61F 2/04
10,779,967 B2 * 9/2020 Walsh .................. A61F 2/064
11,039,858 B2 * 6/2021 Albertorio .................. A61B 17/025
11,160,960 B2 * 11/2021 Gray .................. A61B 1/00087
11,596,535 B2 * 3/2023 Folan .................. A61F 2/852
11,998,707 B2 * 6/2024 Walsh .................. A61B 17/12172
12,268,589 B2 * 4/2025 Folan .................. A61F 2/04
12,465,733 B2 * 11/2025 Gray .................. A61M 27/002
12,551,328 B2 * 2/2026 Folan .................. A61F 2/064
12,564,505 B2 * 3/2026 Karavany .................. A61F 2/06
2008/0015671 A1 * 1/2008 Bonhoeffer .................. A61F 2/2418 623/1.2
2009/0192588 A1 * 7/2009 Shin .................. A61F 2/04 623/1.38
2011/0093002 A1 * 4/2011 Rucker .................. A61F 2/90 606/198
2013/0012969 A1 * 1/2013 Shin .................. A61F 2/064 606/155
2013/0090714 A1 4/2013 McHugo
2015/0374383 A1 12/2015 Bodewadt et al.
2018/0361127 A1 12/2018 Gray et al.
2019/0099589 A1 4/2019 Walsh et al.
2019/0125558 A1 * 5/2019 Coyne .................. A61F 2/2412
2019/0298559 A1 * 10/2019 Gupta .................. A61B 17/1114
2019/0298560 A1 10/2019 Belhe et al.
2021/0307943 A1 10/2021 Gupta et al.
2023/0149195 A1 * 5/2023 Folan .................. A61F 5/0079 604/8

* cited by examiner

DEVICES, SYSTEMS, AND METHODS FOR ENGAGEABLE STENTS

CROSS-REFERENCE TO RELATED APPLICATIONS

This application claims the benefit of priority of U.S. Provisional Application No. 63/307,775, filed Feb. 8, 2022, the entire disclosure of which is hereby incorporated by reference herein for all purposes.

FIELD

The present disclosure relates generally to the field of medical devices. In particular, the present disclosure relates to medical devices for facilitating or restricting the flow of fluids and materials along one or more body lumens, such as one or more stents.

BACKGROUND

Placement of a self-expanding stent within an anatomical area (e.g., body lumen, passage, vessel, duct, etc.) may enable fluid communication or restriction from one area to another. For example, a stent may restrict or promote flow of material across a diseased sphincter.

However, available stents may carry various disadvantages. For example, stents may be more likely to dislodge or migrate from a desired placement, such as in response to forces generated by a patient's motion or may fail to provide enough or may provide too much retentive strength for a given use. Additionally, stents may need to be removed and/or replaced after substantial ingrowth with the patient, risking trauma to the stent site upon removal/replacement.

Accordingly, a variety of advantageous medical outcomes may be realized by the devices, systems, and methods of the disclosure.

SUMMARY

In one aspect, a system of stents may comprise an outer stent comprising an elongate body configured to be expandable between a constrained configuration and an unconstrained configuration. The elongate body in the unconstrained configuration may include a retention member and a cylindrical saddle region adjacent the retention member. The cylindrical saddle region may define a lumen extending along a longitudinal axis of the outer stent. The retention member of the outer stent may comprise a double-walled flange having an axially inward wall, an axially outward wall, and a radial wall extending therebetween. An inner stent of the system may comprise an elongate body configured to be expandable between a constrained configuration and an unconstrained configuration. The elongate body in the unconstrained configuration may include a retention member and a cylindrical saddle region adjacent the retention member. The cylindrical saddle region may define a lumen. The retention member of the inner stent may comprise a double-walled flange having an axially inward wall, an axially outward wall, and a radial wall extending therebetween. The axially inward wall of the retention member of the inner stent may be configured to removably engage the axially outward wall of the retention member of the outer stent.

In the described and other aspects of the present disclosure, the axially inward wall of the retention member of the inner stent and the axially outward wall of the retention member of the outer stent may each comprise a concave surface. The axially outward wall of the retention member of the inner stent member and the axially inward wall of the retention member of the outer stent may each comprise a convex surface. The retention member of the outer stent may be located at a distal portion of the elongate body. The retention member of the inner stent may be located at a proximal portion of the elongate body. A longitudinal cross-sectional profile of the retention member of the inner stent may substantially match a longitudinal cross-sectional profile of the retention member of the outer stent. The axially outward wall of the retention member of the inner stent may extend to a flexible sleeve contiguous with the lumen of the outer stent. A diameter of the cylindrical saddle region of the inner stent may be different than a diameter of the cylindrical saddle region of the outer stent. The radial wall of the outer stent may comprise a diameter greater than a diameter of the cylindrical saddle region of the outer stent. The elongate body of the outer stent may comprise a braid. The cylindrical saddle region of the outer stent may be twisted to a reduced diameter portion. A flexible band may be disposed about the saddle region of the outer stent at a reduced diameter portion. The radial wall of the outer stent may comprise a diameter greater than a diameter of the radial wall of the inner stent. A covering, such an ingrowth promoting cylindrical covering, may extend at least partially along a length of the elongate body of the outer stent. A radiopaque marker may be at each of the retention member of the inner stent and the retention member of the outer stent. The inner stent may further comprise an element configured for reducing a profile of the inner stent and removing the inner stent from the outer stent. A flexible sleeve may be coupled to the inner stent and may extend axially away from the retention member of the outer stent.

In one aspect, a stent may include an elongate body configured to be expandable between a constrained configuration and an unconstrained configuration. The elongate body in the unconstrained configuration may include a proximal retention member and a cylindrical saddle region adjacent the proximal retention member. The cylindrical saddle region may define a lumen along a longitudinal axis of the stent. The proximal retention member may comprise a double-walled flange having an axially inward wall comprising a concave surface, an axially outward wall, and a radial wall extending therebetween. The proximal retention member may be configured to reversibly engage a retention member of another device.

In the described and other aspects of the present disclosure, a distal retention member may be distal to the cylindrical saddle region. The distal retention member may comprise a double-walled flange having an axially outward wall comprising a concave surface, an axially inward wall, and a radial wall extending therebetween. The lumen of the cylindrical saddle region may reduce from a larger diameter at each of the proximal retention member and the distal retention member to a smaller diameter along the cylindrical saddle region.

In one aspect, a method of delivering a stent system may include delivering an outer stent comprising a retention member and a lumen extending through the outer stent into a body lumen of a patient. An inner stent comprising a retention member may be delivered within the lumen of the outer stent such that the retention member of the inner stent is positioned within and removably engaged with the retention member of the outer stent. The inner stent may be removed from the outer stent. Ingrowth may be allowed between the outer stent and the body lumen, as an inner stent may instead be removed or replaced while the outer stent may be stationed within the patient for longer periods than the inner stent. The outer stent may be delivered into a body lumen that is the pyloric sphincter, and the inner stent may be extended along the duodenum. An inner stent may include an element that may be grasped and twisted, thereby constraining the inner stent for removal from engagement with the outer stent. The inner stent may be delivered through the outer stent such that a portion of the inner stent extends distally beyond a distal end of the outer stent.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component in each embodiment of the disclosure shown where illustration is not necessary to allow those of skill in the art to understand the disclosure. In the figures.

DETAILED DESCRIPTION

Figure 1A:
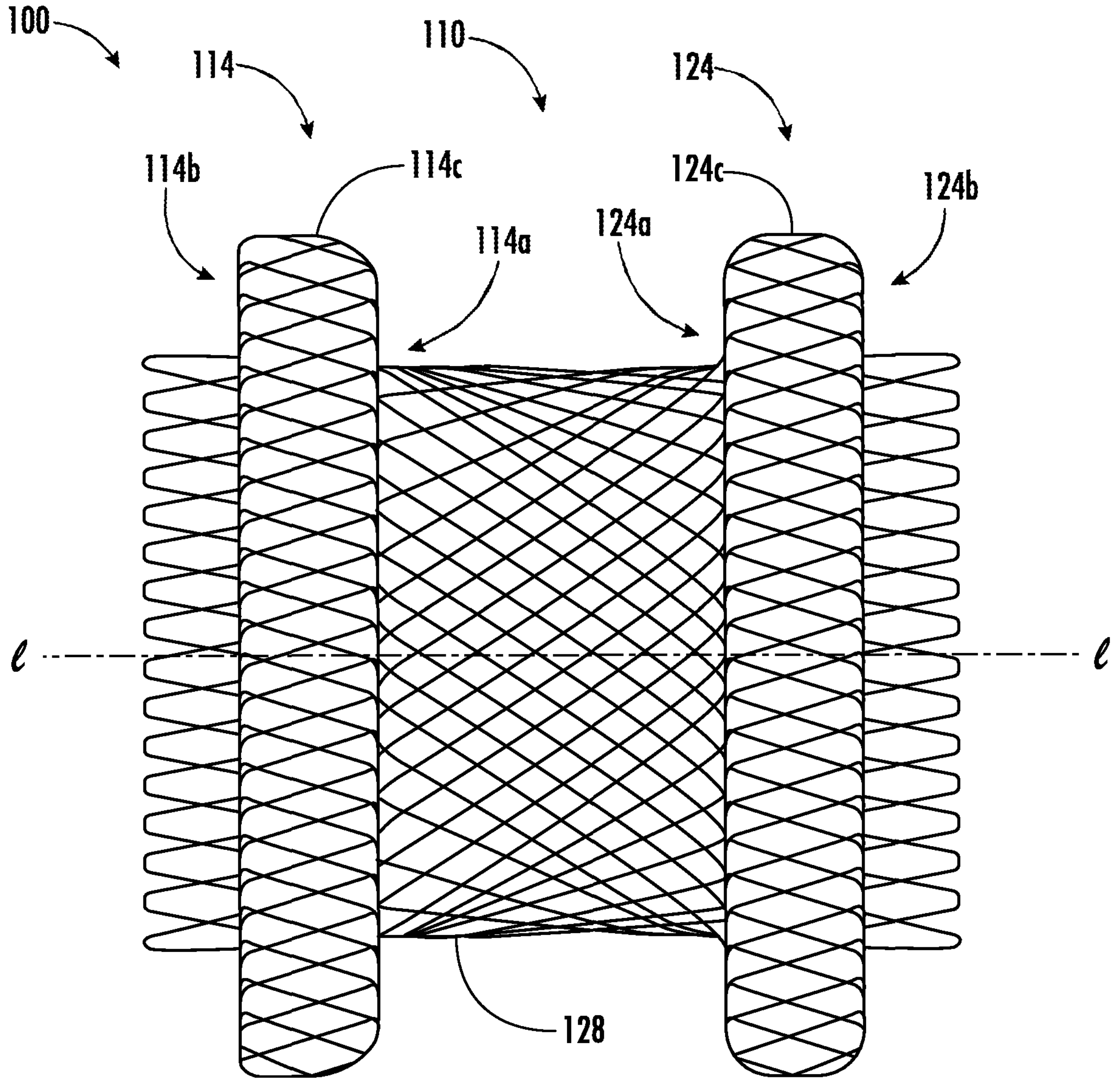
FIG. 1A illustrates a side view of an outer stent, according to an embodiment of the disclosure.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs. The detailed description should be read with reference to the drawings, which are not necessarily to scale, depict illustrative embodiments, and are not intended to limit the scope of the invention.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this disclosure and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

Although embodiments of the present disclosure are described with specific reference to medical devices (e.g., stents) and systems for restriction or drainage of the gallbladder, pseudocysts, gastrojejunostomy, and/or the like, it should be appreciated that such medical devices may be used in a variety of medical procedures (e.g., external biliary drain conversion, enteroenterostomy, gastroduodenostomy and gastroileostomy, etc.) to establish and/or maintain a temporary or permanent restriction or open flow passage from, along, or between a variety of body organs, lumens, ducts, vessels, fistulas, cysts and spaces (e.g., the dermis, stomach, duodenum, jejunum, small intestine, gallbladder, kidneys, pancreas, biliary trees, pancreatic trees, bladder, ureter, abscesses, walled-off pancreatic necrosis, bile ducts, etc.). The devices may be inserted via different access points and approaches, e.g., percutaneously, endoscopically, laparoscopically or some combination thereof. The medical devices disclosed herein are self-expanding, but in other embodiments the medical devices may be expandable by other means, including, e.g., a balloon catheter. Moreover, such medical devices are not limited to restriction or drainage, but may facilitate access to organs, vessels, or body lumens for other purposes, such as creating a path to divert or bypass fluids or solids from one location to another, removing obstructions and/or delivering therapy, including non-invasive or minimally invasive manipulation of the tissue within the organ and/or the introduction of pharmacological agents via the open flow passage.

Referring to FIG. 1A, a side view of an embodiment of an outer stent 100 is illustrated, according to an embodiment of the disclosure. The outer stent 100 includes an elongate body 110 expandable between a constrained configuration and an unconstrained configuration. In FIG. 1A, the elongate body 110 is illustrated in the unconstrained configuration. In the unconstrained configuration, the elongate body 110 is radially expandable into a distal retention member 114 and a proximal retention member 124. The elongate body 110 includes a cylindrical saddle region 128 adjacent the retention members 114, 124. The saddle region 128 defines a lumen extending along a longitudinal axis ℄ of the outer stent 100. Each of the retention members 114, 124 include a double-walled flange having an axially inward wall 114*a*, 124*a*, an axially outward wall 114*b*, 124*b*, and a radial wall 114*c*, 124*c* extending therebetween. The distal and proximal retention members 114, 124 extend radially outward from the longitudinal axis ℄ and from an outer circumference of the elongate body 110 in the unconstrained configuration to define the double-walled flanges with the respective inward wall 114*a*, outward wall 114*b*, inward wall 124*a*, and outward wall 124*b*. The inward wall 114*a* is axially inward along the distal retention member 114, the outward wall surface 114*b* is axially outward along the distal retention member 114, the inward wall 124*a* is axially inward along the proximal retention member 124, and the outward wall 124*b* is axially outward along the proximal retention member 124. The radial wall 114*c* of the distal retention member extends between and connects the inward wall 114*a* and the outward wall 114*b*. The radial wall 124*c* of the proximal retention member 124 extends between and connects the inward wall 124*a* and the outward wall 124*b*. Although the outer stent 100 of FIG. 1A is illustrated with the distal retention member 114 and the proximal retention member 124, a stent described herein may include only one of the distal and proximal retention members 114, 124.

Figure 1B:
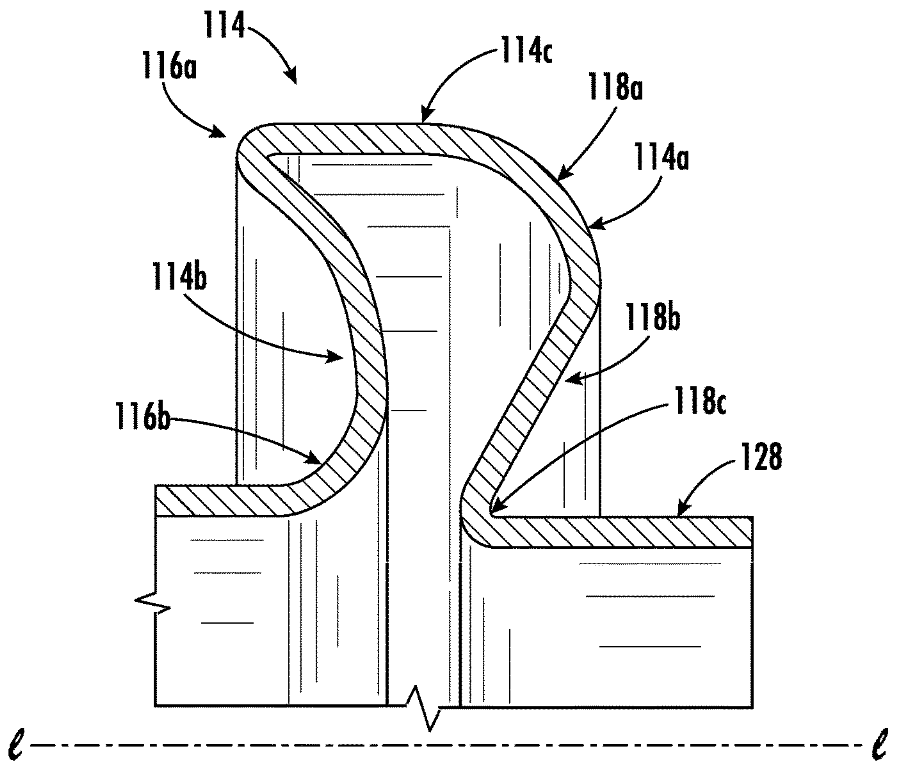
FIG. 1B illustrates an exemplary embodiment of a cross-sectional profile of a retention member, such as for use with the outer stent of FIG. 1A.

Referring to FIG. 1B, an embodiment of an exemplary cross-section of a retention member of a stent is illustrated, such as the distal retention member 114 of the outer stent 100 of FIG. 1A. The retention member 114 includes an outward wall 114*b* that extends from a radial wall 114*c*. The outward wall 114*b* includes a first portion 116*a* and a second portion 116*b*. The first portion 116*a* is convex along the outward wall 114*b* extending to the concave second portion 116*b*. The radius of curvature of the first portion 116*a* is smaller than the radius of curvature of the second portion 116*b*. In various embodiments, a radius of curvature of each of the portions 116*a*, 116*b* of the outward wall 114*b* may be less than, greater than, or equal to each other depending on the procedure desired. The inward wall 114*a* is convex where it extends from the radial wall 114*c* to a first portion 118*a* until it further extends to a straight section at a second portion 118*b*, which is at an angle less than 90 degrees from the longitudinal axis ℄. The first portion 118*a* has a radius of curvature that is larger than the first portion 116*a* of the outward wall 114*b*. The second portion 118*b* extends to a third portion 118*c* of the inward wall 114*a*, where the distal retention member 114 connects with the saddle region 128. One or more convex and/or concave portions may include the same or various angles of completion of curvature, radii of circumference, lengths, other features, or any combination thereof.

In various embodiments, one or more stents are configured to extend along, across, or between one or more lumens and may assist with apposing tissue layers (e.g., muscularis layers), restricting flow, and/or promoting flow temporarily or permanently. One or both of first and second retention members at opposing ends of a stent, as described herein may be double-walled and include one or more perpendicular or non-perpendicular surfaces of an axially inward and axially outward wall of the retention member. The walls may be oriented with respect to a cylindrical saddle region extending along a longitudinal axis between the flanges. Such configurations of non-perpendicular surfaces may help to reduce migration of the stent with respect to the tissue(s) or another stent (e.g., an inner stent at least partially within an outer stent), when compared, for example, to a corresponding retention member with perpendicular surfaces. Additionally, or alternatively, retention members, as double-walled flanges with one or more non-perpendicular surfaces, may be configured to provide more resistance of the device being pulled out of its intended placement once deployed, e.g., resulting in higher pull-out forces as compared to a corresponding retention member with perpendicular surfaces. For example, a double-walled flange with non-perpendicular surfaces may have a pull-out force above about 4 N, 4.5 N, 5 N, 5.25 N, 5.5 N, 5.75 N, or 6 N, such as a pull-out force of about 4.1 N, 4.2 N, 4.3 N, 4.4 N, 4.5 N, 4.6 N, 4.7 N, 4.8 N, 4.9 N, 5.0 N, 5.1 N, 5.2 N, 5.3 N, 5.4 N, 5.5 N, 5.6 N, 5.7 N, 5.75 N, 5.8 N, 5.9 N, 6.0 N, 6.1 N, 6.2 N, 6.3 N, 6.4 N, 6.5 N, 6.6 N, 6.7 N, 6.8 N, 6.9 N, 7.0 N, 7.1 N, 7.2 N, 7.3 N, 7.4 N, 7.5 N, 7.6 N, 7.7 N, 7.8 N, 7.9 N, 8.0 N, 8.1 N, 8.2 N, 8.3 N, 8.4 N, 8.5 N, 8.6 N, 8.7 N, 8.8 N, 8.9 N, 9.0 N, 9.5 N, 10 N, 11 N, 12 N, 13 N, 14 N, 15 N, 20 N, 25 N, or the like. In various embodiments, one or more non-perpendicular surfaces may also be configured to interact less traumatically with at least one tissue wall of first and second body lumens (e.g., configuring an inward wall with a point of tissue contact having less surface area), as compared, for example, to a perpendicular surface or to another surface with at least one tissue-engaging element, such as a prong, barb, hook, or other like feature.

Delivering a stent within a patient may result in the stent anchoring and/or indwelling along tissue of the patient. Removal or replacement of such a stent may undesirably traumatize the tissue. It therefore may be desirable to extend the duration of the stent within the patient and instead remove or replace a second stent that is configured to engage the first stent. For example, an outer stent may be delivered into a patient to engage and interface substantially with tissue of the patient, and an inner stent may be delivered at least partially within the outer stent such that the inner stent engages the outer stent. Such a configuration may allow for the inner stent to be removed or replaced from engagement with the outer stent with minimal trauma to the tissue compared to removal or replacement of the outer stent.

Figure 1C:
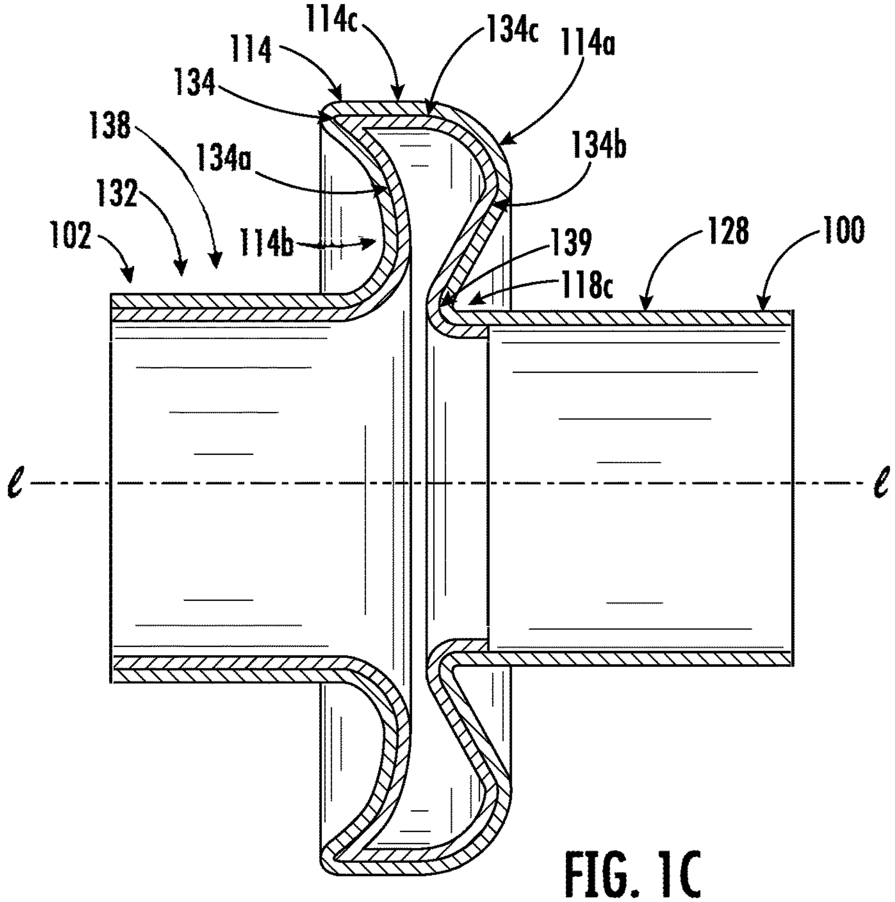
FIG. 1C illustrates an exemplary embodiment of a cross-sectional profile of a retention member of an inner stent engaging an exemplary embodiment of a cross-sectional profile of a retention member of an outer stent, in each case such as the profile of FIG. 1B.

Referring to FIG. 1C, an inner stent 102 is illustrated engaging the outer stent 100 of FIGS. 1A and 1B. The inner stent 102 includes an elongate body 132 configured to be expandable between a constrained configuration and an unconstrained configuration. In FIG. 1C, the elongate body 132 of the inner stent 102 is in the unconstrained configuration including a retention member 134 and a cylindrical saddle region 138 adjacent the retention member 134. The cylindrical saddle region 138 defines a lumen that extends and is in fluid communication with the lumen of the saddle region 128 of the outer stent 100. The retention member 134 of the inner stent 100 includes a double-walled flange having an axially inward wall 134*a*, an axially outward wall 134*b*, and a radial wall 134*c* extending therebetween. The axially inward wall 134*a* of the retention member 134 of the inner stent 102 is removably engaged with the axially outward wall 114*b* of the distal retention member 114 of the outer stent 100.

In various embodiments of a system of stents including an inner stent engaged within an outer stent, one or more walls of a retention member of the outer stent may assist with engaging a retention member of the inner stent. For example, with reference to FIG. 1C, the engaging interface of the concave axially inward wall 134*a* of the retention member 134 of the inner stent 102 with the concave axially outward wall 114*b* of the distal retention member 114 of the outer stent 100 may increase resistance and a threshold force for the inner stent 102 to disengage from the outer stent 100 compared to perpendicular walls (with respect to the longitudinal axis ℄). In various embodiments, one or more portions of the retention member 134 of the inner stent 102 may match (e.g., compliment, align, engage, mimic, coincide, couple, or the like) one or more portions (e.g., at least a portion of a cross-sectional profile) of the distal retention member 114 of the outer stent 102. For example, the axially inward wall 134*a* may match the axially outward wall 114*b*. Additionally, a portion of a retention member, such as the portion 118*c* of the distal retention member 114, for example, may resist inward radial movement of a retention member (e.g., retention member 134) out of the distal retention member 114 by engaging (e.g., keying or interfacing) with at least a portion (e.g., portion 139) of the retention member 134. Additionally, an axial wall of a retention member, such as the axially inward wall 114*a* of the distal retention member 114, for example, may accept and provide flexing room for a retention member (e.g., retention member 134) to engage the distal retention member 114. Once engaged, the retention members 114, 134 may have a fit with each other such that the surfaces of the retention members 114, 134 are in complete or substantially complete contact with each other, e.g., to resist movement and/or slippage with respect to each other.

In various embodiments, an inner stent may comprise one or more retention members. In embodiments of an inner stent including a single retention member, an elongate body of the stent may extend away from the single retention member forming a lumen within a flexible sleeve and/or saddle region, e.g. along a body lumen such as the duodenum. The sleeve may be inverted after or during delivery of an inner stent within an outer stent, e.g., delivering an inner stent to engage a distal retention member of an outer stent and inverting the sleeve along the outer stent such that the sleeve extends proximally from the outer stent (such as in the colon or small intestine).

In various embodiments, a diameter of a retention member may be within the range of about 5 mm to about 40 mm. Other exemplary retention member diameters may be within a range of about 15 mm to about 40 mm, about 15 mm to about 35 mm, or the like. In various embodiments, a diameter of a retention member may be set to have a particular offset from a diameter of the cylindrical saddle region in the unconstrained configuration. For example, stents may be configured to include about 3 mm to about 20 mm difference between a diameter of the cylindrical saddle region and a diameter of the first retention member and/or a second retention member in the unconstrained configuration. In other examples, the first retention member and/or the second retention member may be configured to have a diameter that is about 1 to about 5 times greater than the diameter of the cylindrical saddle region in the unconstrained configuration. For example, for a device with the cylindrical saddle region having a diameter of about 10 mm in an unconstrained configuration, the first retention member and/or a second retention member may have a diameter of about 13 mm to about 30 mm, about 15 mm to about 25 mm, or about 16 mm to about 20 mm. In another example, a stent with the cylindrical saddle region in the unconstrained configuration having a diameter of about 20 mm may have one or more retention members with a diameter of about 23 mm to about 40 mm. It will be understood that some embodiments may include greater or lesser offsets between the diameter of the cylindrical saddle region and the larger diameter of the first retention member and/or the second retention member. In various embodiments, a retention member may have an axial width substantially the same or different than another retention member of the same or a different stent. An axial width of a retention member may be measured as a distance along the longitudinal axis between an axially inward wall and an axially outward wall of a respective retention member, inclusive of the radial wall. In various embodiments, a width of a retention member in an unconstrained configuration may be about 0.5 mm to about 10.0 mm. Other embodiments may include a smaller and/or greater width of one or more retention members, such about 0.5 mm to about 6 mm, about 2 mm to about 6 mm, or about 3 mm to about 7 mm. In some embodiments, a retention member may have a constant width. In other embodiments, a width of a retention member may vary along a vertical plane (i.e., perpendicular with a longitudinal axis of the elongate body of a stent). Various embodiments may include total stent lengths ranging, e.g., from about 5 mm to about 60 mm in the unconstrained configuration. For example, exemplary deployed stents may have lengths of about 10 mm to about 50 mm, about 10 mm to about 35 mm, or the like. A ratio of diameters between a retention member and an adjacent saddle region or elongate body may be larger if it is desirable to require a larger pullout force for removing a stent, or a ratio of diameters between a retention member and an adjacent saddle region or elongate body may be smaller if it is desirable to require a smaller pullout force for removing a stent.

In various embodiments, a length of a cylindrical saddle region may be measured as (i) the length along the elongate body between the beginning of axially inward wall(s) of one or more retention members, (ii) the length along the body that is the shortest distance between retention members at any points along the inward walls when the stent is unconstrained, but not deployed along tissue, (iii) the length along the body that is the shortest distance between retention members at any points along the inward walls when the stent is unconstrained and deployed in tissue, or (iv) the length along the body from a point along an inward wall of a single retention member of a stent to an opposing end of the elongate body. In various embodiments, a cylindrical saddle region, including under the conditions (i)-(iv) above, may have a length of about 5 mm to about 150 mm in the unconstrained configuration, about 5 mm to about 35 mm in the unconstrained configuration, or the like. Exemplary lengths of the cylindrical saddle region of stents for gastrointestinal functions in the unconstrained configuration may include lengths of about 10 mm to about 30 mm, about 15 mm to about 20 mm, about 10 mm to about 20 mm, about 10 mm to about 15 mm, about 5 mm to about 10 mm or the like. In many embodiments, a diameter of the cylindrical saddle region in the unconstrained configuration may be greater than a diameter of the elongate body in the constrained configuration. For example, a diameter of the cylindrical saddle region in the unconstrained configuration may be about 3 mm to about 40 mm. In some embodiments, a diameter of the cylindrical saddle region in the unconstrained configuration may be about 5 mm to about 25 mm, about 5 mm to about 20 mm, about 5 mm to about 15 mm, or about 10 mm to about 20 mm, or the like. In various embodiments, the diameter of the cylindrical saddle region may be about 3 to about 5 times greater, about 3 to about 10 times greater, or the like than a corresponding diameter of the elongate body in the constrained configuration.

In various embodiments, an elongate body of a stent may be partially or fully covered, uncovered, coated, or a combination thereof. An elongate body may include a constrained configuration (e.g., unexpanded or delivery configuration), an unconstrained configuration (e.g., foreshortened, expanded, or deployed configuration), and a partially constrained/unconstrained transition between the constrained and unconstrained configurations.

Non-perpendicular surfaces of retention members comprising axially inward and outward walls of double-walled flanges, may include one or more curved portions, straight portions, angled portions, concave portions, convex portions, or any combination thereof. Each portion may include a substantially equal or a different length, angle, radius of curvature, directionality, angle, or other feature with respect to another portion. Surfaces of first retention members and second retention members may be the same or different. For example, each end of a medical device may be designed to improve the strength (e.g., resistance to pull-out or retentive strength, or resistance to radial compression or radial strength) of the stent or a portion of the stent and provide a desired amount of linear apposing force when placed across tissue planes and/or when engaging another stent. Retention member shapes may include one or more rolls and/or structural folds, for example, to create a double-walled flange structure. In various embodiments, retention members may include multiple of inflection points, wherein an inflection point may be a point of a curve at which a change in direction of curvature occurs.

Referring to FIGS. 2A-2D various cross-sectional profiles of a retention member of a stent are illustrated, according to embodiments of the disclosure. A configuration of a retention member as described with respect to FIGS. 2A-2E may be substituted or applied to any of the embodiments described herein. For example, the distal retention member 114 as described with respect to FIG. 1A, the proximal retention member 124 as described with respect to FIG. 1A, the retention member as described with respect to FIG. 1C, and/or other retention members described herein may have a configuration as described with respect to FIGS. 2A-2E. Accordingly, embodiments may comprise multiple retention members with the same or with different configurations.

Figure 2A:
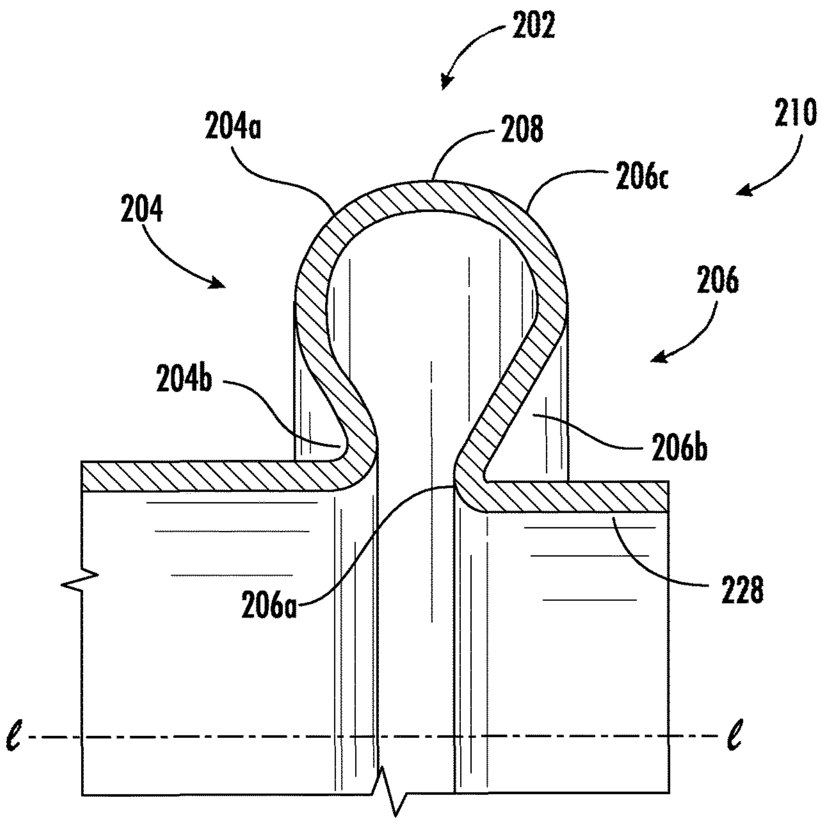
FIG. 2A illustrates a cross-sectional profile of another retention member of a stent, according to an embodiment of the disclosure.

Referring to FIG. 2A, an elongate body 210 includes a retention member 202. The retention member 202 includes a double-walled flange having a first wall 204, a second wall 206 axially offset from the first wall 204 along a longitudinal axis ℓ, and a radial wall 208 extending therebetween. A cylindrical saddle region 228 is adjacent and extends from the first wall 204. The second wall 206 includes three portions: portion 206*a*, portion 206*b*, and portion 206*c*. The cylindrical saddle region 228 may extends to a concave surface of portion 206*a*, which extends to portion 206*b*. The portion 206*b* includes a substantially straight section that extends at an angle of less than 90 degrees from the longitudinal axis ℓ. The portion 206*c* includes a convex curve, which extends between the portion 206*b* and the radial wall 208. The radial wall 208 includes a portion substantially parallel with the longitudinal axis ℓ. The radial wall 208 extends into the first wall 204, which includes a portion 204*a* and a portion 204*b*. The portion 204*a* includes a convex surface having variable radii along its length. One or more convex and/or concave surfaces may include the same or various angles of completion of curvature, radii of circumference, lengths, other feature, or any combination thereof. The portion 204*b* is concave and connects to the remainder of the elongate body 210.

Figure 2B:
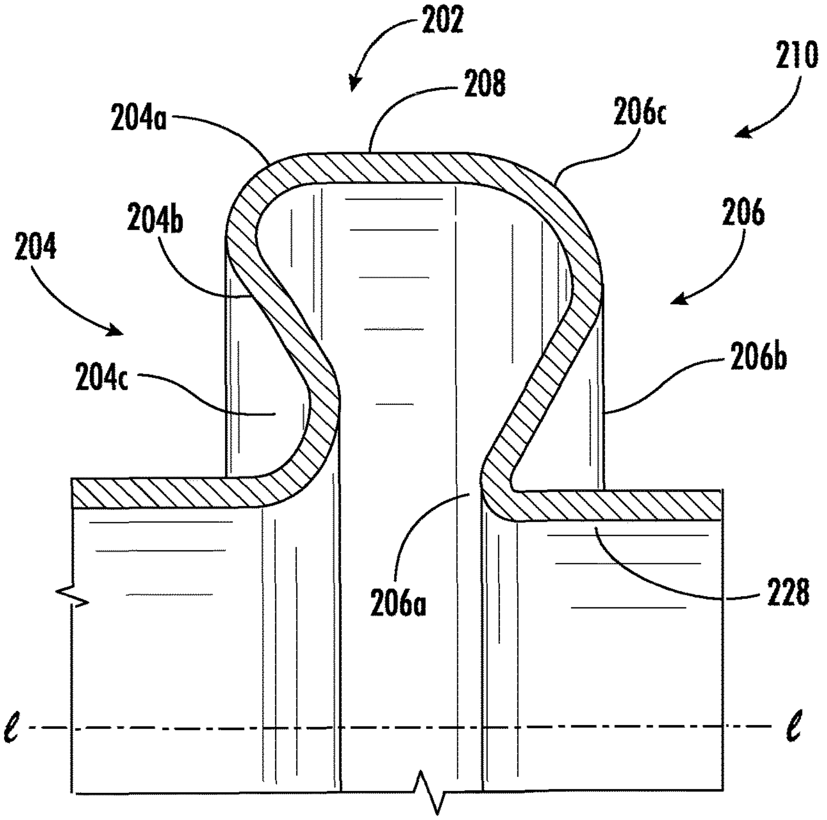
FIG. 2B illustrates a cross-sectional profile of another retention member of a stent, according to an embodiment of the disclosure.

Referring to FIG. 2B, another exemplary embodiment is illustrated, in which a retention member 202 may comprise similar portions 206*a*, 206*b*, and 206*c* as described with respect to FIG. 2A. However, portion 204*a* as illustrated in FIG. 2B may comprise a larger radius of curvature than as illustrated in FIG. 2A. In FIG. 2B, portion 204*b* may comprise a substantially straight section extending from the radial wall 208 and portion 204*a* back towards the cylindrical saddle region 228. The portion 204*b* may extend into a portion 204*c*, which is illustrated in FIG. 2B including a concave portion. Portion 204*c* extends into the remainder of the elongate body 210. Angles of the retention member 202 defined by portions 204*b* and 206*b* are less than 90 degrees with respect to the longitudinal axis ℓ.

Figure 2C:
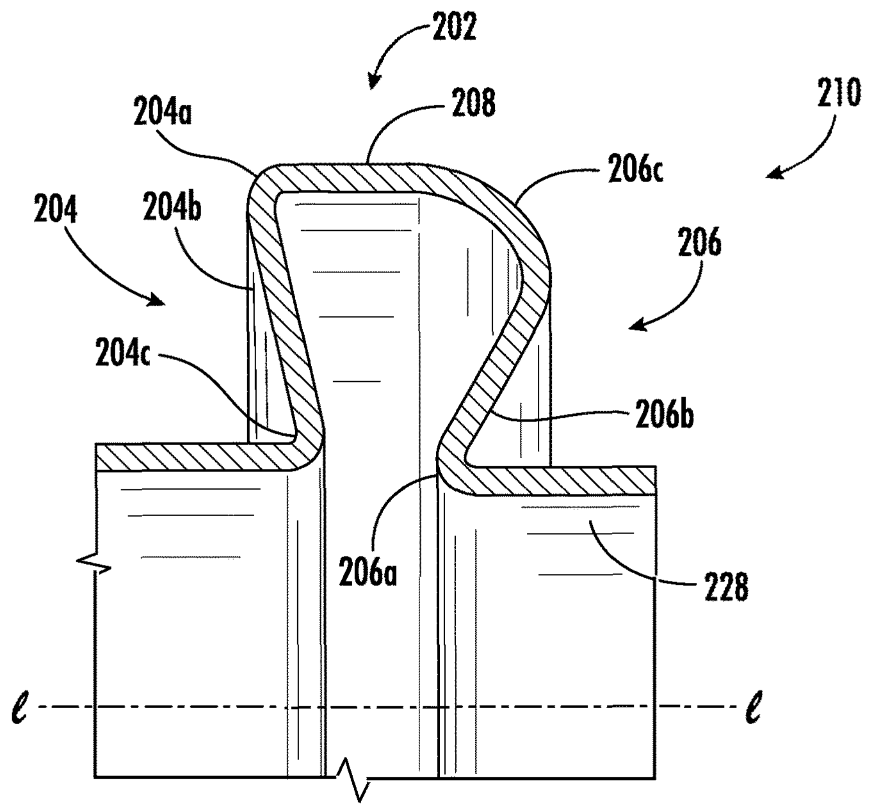
FIG. 2C illustrates a cross-sectional profile of another retention member of a stent, according to an embodiment of the disclosure.

Referring to FIG. 2C, another exemplary embodiment is illustrated, in which a retention member 202 includes the portion 206*a* having a concave curve that extends into a substantially straight section of portion 206*b*. The portion 206*b* extends into a convex curve of portion 206*c*, which in turn extends into the radial wall 208. The radial wall 208 extends into the portion 204*a* having a convex curve. The portion 204*a* extends into a substantially straight section of portion 204*b*, which in turn extends into the portion 204*c* having a concave curve. The substantially straight sections of portions 204*b*, 206*b* are formed at an angle with respect to the longitudinal axis ℓ at less than 90 degrees. The portion 204*c* extends into the remainder of the elongate body 210. However, one or more portions 206*a*, 206*c*, 204*a*, and/or 204*c* may comprise smaller radii of curvature than as illustrated, e.g., as illustrated with respect to the concave curve portion 204*c* in FIG. 2A compared to the concave curve portion 204*c* in FIG. 2C. However, other sections may additionally or instead be interchanged with one or more sections of another embodiment retention members discussed herein. In various embodiments, a concave or convex curve of at least one portion may comprise a small enough radius of curvature to comprise a crease or other fold.

Figure 2D:
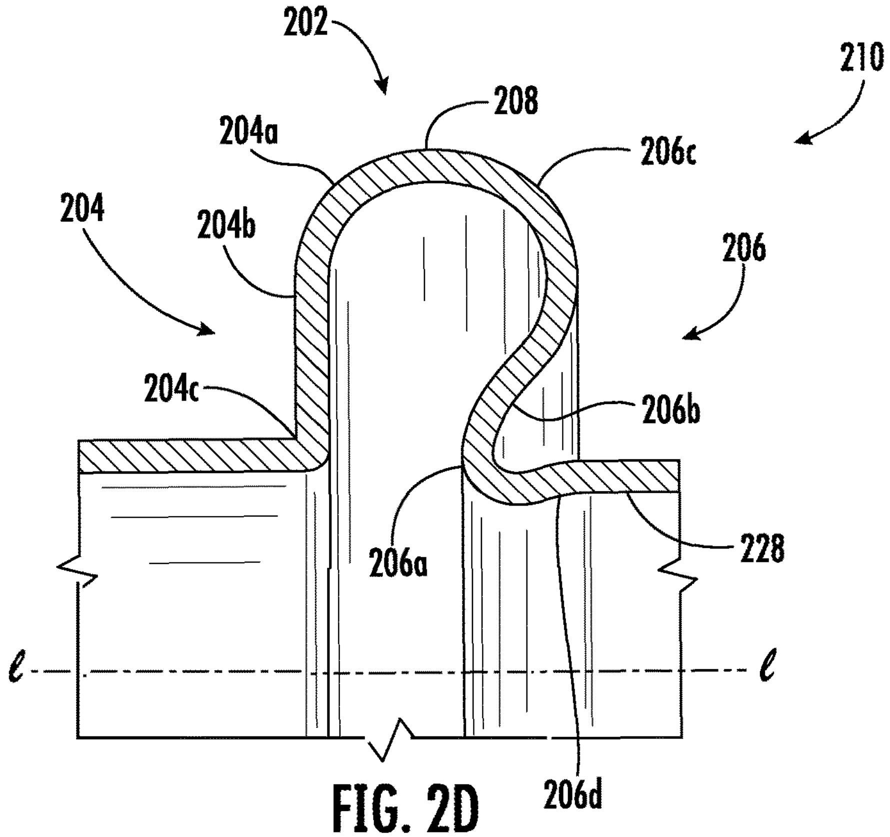
FIG. 2D illustrates a cross-sectional profile of another retention member of a stent, according to an embodiment of the disclosure.

Referring to FIG. 2D, another exemplary embodiment is illustrated, in which a retention member 202 includes similar portions 206*a*, 206*b*, and 206*c* as described with respect to at least one of FIGS. 2A-2C. Portion 206*a*, as illustrated in FIG. 2D, includes a larger radius of curvature than as illustrated in portion 206*a* of FIG. 2A. For example, the portion 206*a* as illustrated in FIG. 2D, may include a radius of curvature of about 1 mm to about 3 mm. In various embodiments, portion 206*a* and/or 206*c* may include a radius of curvature of about 1.5 mm to about 2.1 mm. In FIG. 2D, the portion 206*a* may include varying radii of curvature along its length. As illustrated in FIG. 2D, the portion 206*a* extends radially towards the longitudinal axis ℓ away from the saddle region 228 such that a section of the portion 206*a* is closer to the longitudinal axis ℓ than the cylindrical saddle region 228. A portion 206*d* extends between the saddle region 228 and the portion 206*a*. In various embodiments, portion 206*a* or other portions 206*b*, 206*c*, 206*d* may comprise a non-uniform and/or otherwise undulating curve. Portion 204*b* of the first wall 204, as illustrated in FIG. 2D, includes a straight portion substantially perpendicular to the longitudinal axis ℓ. Portion 204*c* includes a concave surface extending into the remainder of the elongate body 210.

While various profiles of retention members are described with respect to FIGS. 2A-2D, it will be appreciated that various embodiments may comprise one or more similarities and/or differences from the illustrated examples. For example, a first wall 204 or a second wall 206 may be made up of additional or fewer portions, and any portion thereof may comprise a concave section, a convex section, a substantially straight section, or any combination thereof. A portion may extend toward a first or second end of the elongate body, perpendicular to a longitudinal axis, parallel to a longitudinal axis, at another angle with respect to a longitudinal axis, or any combination thereof. Furthermore, dimensions and/or orientations of any of the portions described with respect to FIGS. 2A-2D may be applied to other portions described therewith, alternatively or in combination, or with portions and/or retention member profiles otherwise within the scope of the present disclosure.

In various embodiments, smaller radii of curvature of portions may contribute to a higher retentive strength and/or resistance of the corresponding retention member. For example, the retention member configuration illustrated in FIG. 1B may have a greater resistance to deformation than the respective configuration of FIG. 2A. Accordingly, embodiments may be configured in accordance with various retention member strength and/or resistance requirements as necessitated by at least one particular procedure, tissue, stent engagement, stent function, or other consideration.

In various embodiments, a stent, may be formed of one or more filaments and/or surfaces. In various embodiments, one or multiple metal wires, braids of one or multiple wires, polymeric filaments, sheets, or a combination thereof may form a stent. A stent may include one or more structural elements such as a strut, hoop, mesh, tessellating cell, or other unit. In many embodiments, a stent may comprise a mesh, weave, and/or knit surface. A stent may be formed, in various embodiments, of a shape memory material, such, e.g., as nitinol. Portions or entire features (e.g., a retention member, a saddle region, etc.) of a stent may include a radiopaque marker such that a user may identify locations of one or more features across one or more stents. For example, any portion of a retention member of an inner stent may be radiopaque along with any portion of a retention member of an outer stent such that a user may identify their locations with respect to each other during delivery and deployment to ensure desirable engagement/configuration between the two.

Various stent embodiments described herein may include a full or partial covering, coating, or other membrane over an interior, over an exterior of the devices, extending between structural elements, or any combination thereof. For example, a covering, coating, or other membrane may comprise silicone, a polymer, or a combination thereof. For example, a cover may comprise polyurethane, polytetrafluoroethylene, expanded polytetrafluoroethylene, polyvinylidene fluoride, an aromatic polycarbonate-based thermoplastic urethane, and/or other like materials. A covering may include ingrowth promoting materials for interfacing with tissue. A covering may be applied by dip coating, roll coating, painting, spraying, other known disposition method, or a combination thereof. A covering, coating, or other membrane may inhibit tissue growth and/or minimize fluid leakage from within and/or without the stent. A first retention member, a second retention member, a saddle region extending between the first retention member and the second retention member, or a combination thereof may include a solid covering, a porous covering, or other configuration of covering. In various embodiments, a circumferential covering or coating may be applied to cover the full length of the stent, or a partial length of the stent. For example, a partial coating may cover the full length of the saddle region, but not the flanges or vice versa.

Various embodiments described herein may comprise one or more additional features designed to engage at least one tissue layer. For example, embodiments may include one or more textured surfaces, prongs, or other tissue-engaging elements along one or more retention members.

Various embodiments herein may include a retention member and an alternative configuration at an opposing end or portion of a stent. For example, various embodiments may include a flange with walls perpendicular to a longitudinal axis, a flared retention member, a bulbous retention member, a ramped retention member, a curled retention member, a folded retention member, or another configuration. Several embodiments may include one or more components for managing material flow therethrough. For example, various embodiments may include a valve, barrier member, funnel, tube, reducer, or other structure useful for managing a flow therethrough.

In various embodiments of a medical device, at least a portion of one or more walls of a retention member may include at least one curved section, straight section, section angled with respect to a longitudinal axis, section perpendicular to a longitudinal axis, section parallel to a longitudinal axis, a radius of curvature, or any combination thereof. Although cross-sectional profiles of retention members are illustrated and described herein with a particular orientation, it will be appreciated that any retention member may be inverted, flipped, or mirrored in orientation (e.g., across an "x" (horizontal) or "y" (vertical) axis of a figure of the disclosure) depending on the procedure, e.g., for endoscopy procedures, colonoscopy procedures, desired engagement between retention member(s) and tissue or other retention member(s), atraumatic concerns during delivery, deployment, or removal, or the like.

Figure 3:
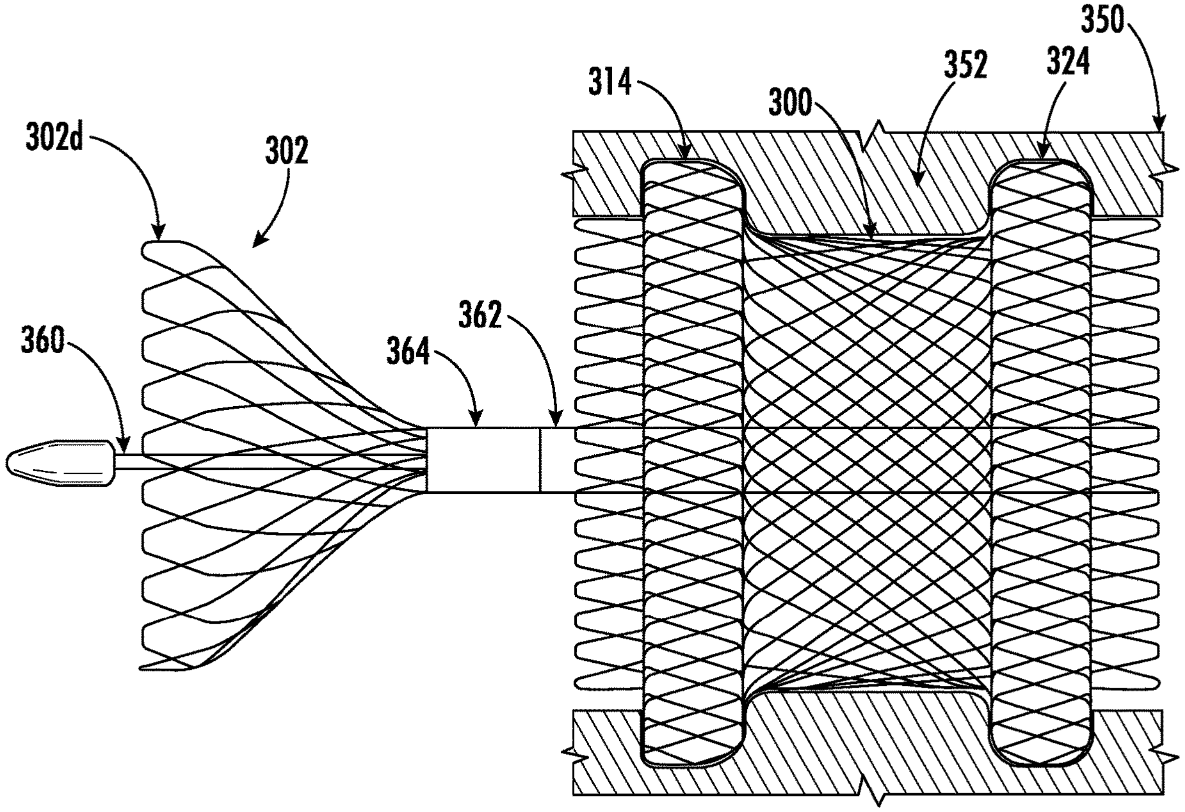
FIG. 3 illustrates a system of stents being delivered into a patient, according to an embodiment of the disclosure.

With reference to FIG. 3 a system of stents is illustrated being delivered into a patient, according to an embodiment of the disclosure. An outer stent 300 is deployed along patient tissue 350, which may extend across an opening in a tissue wall or apposed tissue walls, e.g., a sphincter 352, such as the pylorus sphincter. The outer stent 300 may have been delivered in a constrained configuration along a guidewire 360 while being constrained by a retractable sheath 362, which may include a radiopaque marker 364 at a distal end of the sheath 362. The sheath 362 may have been retracted to deploy the outer stent 300 along the tissue 350 in an unconstrained configuration such that a distal retention member 314 and a proximal retention member 324 may engage with the tissue 350. With the outer stent 300 deployed as illustrated in FIG. 3, the guidewire 360 and the sheath 362 may be extended through the outer stent 300 for delivery of the inner stent 302 in a constrained configuration over the guidewire 360 and constrained by the sheath 362 (although the inner stent 302 could be delivered and deployed using another guidewire and/or sheath). The distal ends of the guidewire 360 and the sheath 362 are extended distally beyond the outer stent 300 for deployment of the inner stent 302. The inner stent 302 is being partially unconstrained by proximally retracting the sheath 362 with respect to the guidewire 360. A distal portion **302*d* of the inner stent 302 is unconstrained while a proximal portion of the stent 302 is constrained by and within the sheath 362. The proximal portion of the stent, including a retention member, may be unconstrained within the outer stent 300 such that the retention member engages the distal retention member 314 of the outer stent 300, e.g., as illustrated in FIG. 1C with the retention member 134 of the inner stent 102** engaging the distal retention member 114 of the outer stent 100. Although FIG. 3 is illustrated/described as deploying the inner stent 302 to engage only the distal retention member 314 of the outer stent 300, in various embodiments the inner stent 302 may include two retention members to engage each one of the distal and proximal retention members 314, 324 of the outer stent. Although FIG. 3 is illustrated/described as partially deploying the inner stent 302 distally beyond the outer stent 300, the inner stent 302 may be deployed at least partially proximal of the outer stent 300 (e.g., within the colon or small intestines), or the inner stent 302 may be deployed entirely within the outer stent 300 (e.g., to engage both the distal and proximal retention members 314, 324 of the outer stent 300).

Figure 4A:
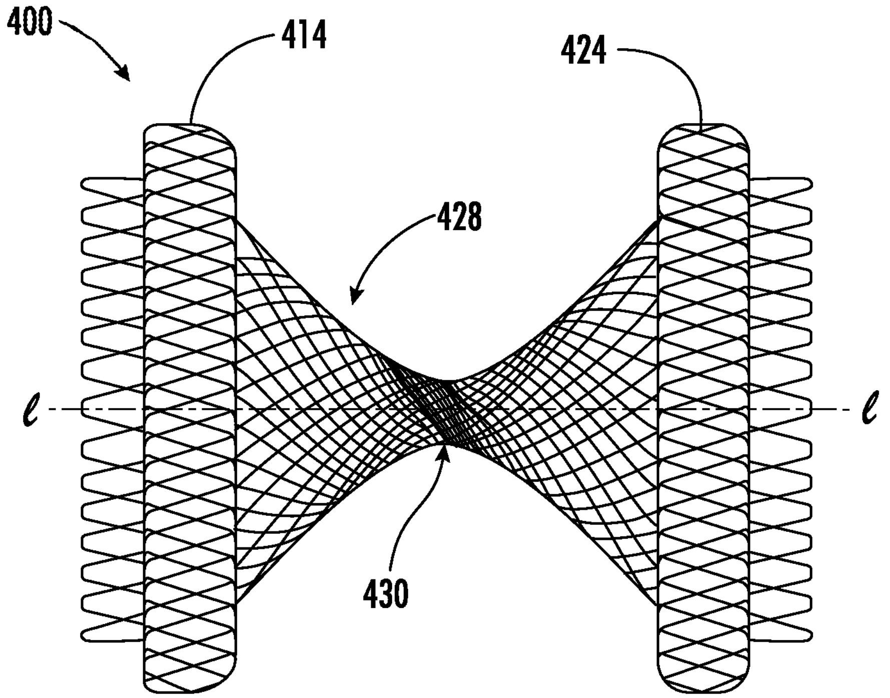
FIG. 4A illustrates a stent that is twisted to a reduced diameter portion, according to an embodiment of the disclosure.

With reference to FIG. 4A, a stent 400 is illustrated including a twist 430 along its saddle region 428, according to an embodiment of the present disclosure. The saddle region 428 is reduced in diameter from each of the distal retention member 414 and the proximal retention member 424 towards the twist 430 along a longitudinal axis ℓ. The stent 400 is illustrated in an unconstrained configuration. The twist 430 may be expandable, e.g., such that another device such as a guidewire, a catheter, and/or another stent, or the like may be extended through the twist 430 of the unconstrained stent 400 as the saddle region 428 partially untwists or otherwise expands to accommodate a diameter of the additional device(s). The twist 430 may substantially return to the configuration illustrated with removal of the device(s) from within the saddle region 428. Additionally, or in the alternative, the twist 430 may function as a reducer/restrictor for flow along the longitudinal axis ℓ and may include a coating and/or covering. It will be appreciated that the stent 400 could be an outer stent or an inner stent as described herein. For example, the stent 400 could be deployed along tissue and an inner stent could be deployed within the stent 400 or the stent 400 could be deployed within an outer stent. The reduced diameter portion of the saddle region 428 may be larger or smaller depending on flow reduction, occlusion, body lumen patency, size of devices to extend therethrough, or fit of the saddle region 428 about a device.

Figure 4B:
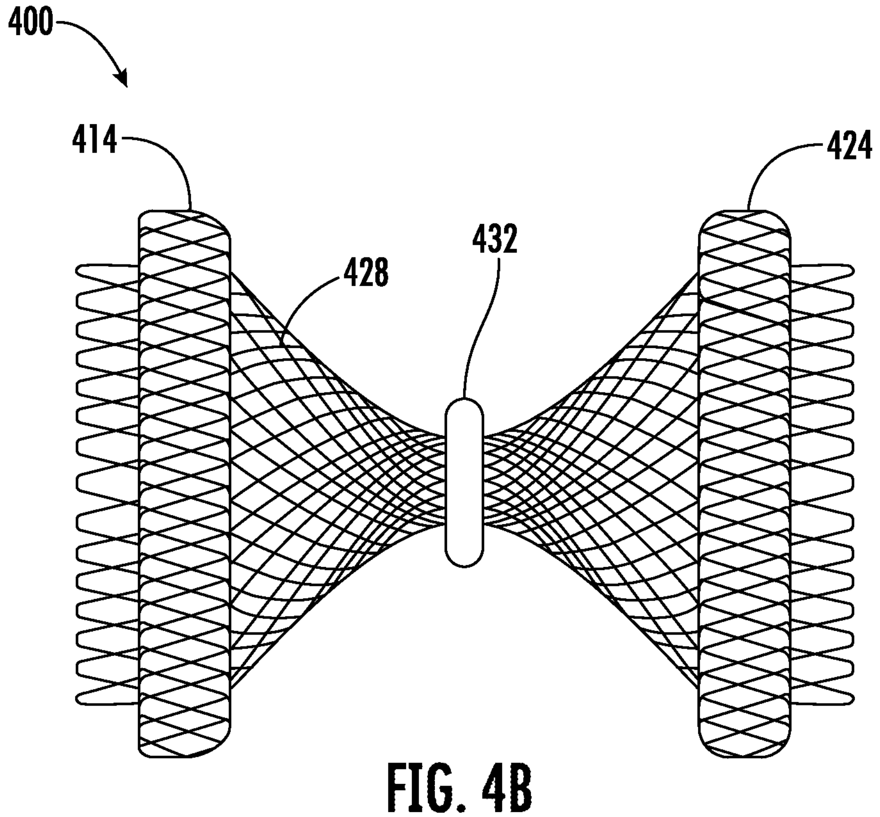
FIG. 4B illustrates a stent including a flexible band at a reduced diameter portion, according to an embodiment of the disclosure.

With reference to FIG. 4B, a saddle region 428 of a stent 400 may be similarly reduced in diameter with a band 432 rather than the twist 430 of FIG. 4A. As illustrated in FIG. 4B, the saddle region 428 is reduced in diameter from each of the distal and proximal retention members 414, 424 towards the band 432 along the longitudinal axis ℓ. Although the stent 400 is illustrated in an unconstrained configuration, the band 432 constrains a portion of the saddle region 428. The band 432 may be flexible such that another device may be extended through the saddle region 428 to expand the saddle region 428 and the band 432 about the device. The band 432 and the saddle region 428 may substantially return to the configuration illustrated in FIG. 4B with removal of the device from within the saddle region 428. Additionally, or in the alternative, the band 432 may function as a reducer/restrictor for flow along the longitudinal axis ℓ and may include a coating and/or covering. It will be appreciated that the stent 400 could be an outer stent or an inner stent as described herein. For example, the stent 400 could be deployed along tissue and an inner stent could be deployed within the stent 400 or the stent 400 could be deployed within an outer stent. The reduced diameter portion of the saddle region 428 may be larger or smaller depending on flow reduction, occlusion, body lumen patency, size of devices to extend therethrough, or fit of the saddle region 428 about a device.

Embodiments of methods of delivering a stent system disclosed herein may include delivering an outer stent comprising a retention member and a lumen extending through the outer stent into a body lumen of a patient. An inner stent comprising a retention member may be delivered within the lumen of the outer stent such that the retention member of the inner stent is positioned within and removably engages the retention member of the outer stent. The inner stent may be removed from the outer stent. Ingrowth may be allowed between the outer stent and the body lumen, as an inner stent may instead be removed or replaced while the outer stent may be stationed within the patient for longer periods than the inner stent. The outer stent may be delivered into a body lumen that is the pyloric sphincter, and the inner stent may be extended along the duodenum. An inner stent may include an element (e.g., a band, a suture, a string, a wire, or the like) that may be grasped and twisted, thereby constraining the inner stent (e.g., to disengage the inner stent from the retention member(s) of the outer stent before removal). An inner stent may be removed from an outer stent in various ways such as by grasping the inner stent or an element coupled to the inner stent (e.g., a suture, a loop, a wire, etc.) with a device (e.g., forceps, grasper, clamp, etc.) and separating the inner stent from the outer stent by pulling, pushing, and/or twisting the device. The inner stent may be delivered through the outer stent.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system of stents, comprising:

an outer stent comprising:

an elongate body configured to be expandable between a constrained configuration and an unconstrained configuration, the elongate body in the unconstrained configuration including a retention member and a cylindrical saddle region adjacent the retention member, the cylindrical saddle region defining a lumen extending along a longitudinal axis of the outer stent;

wherein the retention member of the outer stent comprises a double-walled flange having an axially inward wall extending radially outwardly from the longitudinal axis of the outer stent, an axially outward wall extending radially outwardly from the longitudinal axis of the outer stent, and a radial wall extending circumferentially around the longitudinal axis of the outer stent and between the axially inward wall and the axially outward wall; and an inner stent comprising:

an elongate body configured to be expandable between a constrained configuration and an unconstrained configuration, the elongate body in the unconstrained configuration including a retention member and a cylindrical saddle region adjacent the retention member, the cylindrical saddle region defining a lumen;

wherein the retention member of the inner stent comprises a double-walled flange having an axially inward wall, an axially outward wall, and a radial wall extending therebetween;

wherein the axially inward wall of the retention member of the inner stent is configured to removably engage the axially outward wall of the retention member of the outer stent.

2. The system of claim 1, wherein the axially inward wall of the retention member of the inner stent and the axially outward wall of the retention member of the outer stent each comprise a concave surface curving about an axis oblique to the longitudinal axis of the associated stent.

3. The system of claim 1, wherein the axially outward wall of the retention member of the inner stent member and the axially inward wall of the retention member of the outer stent each comprise a convex surface curving about an axis oblique to the longitudinal axis of the associated stent.

4. The system of claim 1, wherein the retention member of the outer stent is located at a distal portion of the elongate body and wherein the retention member of the inner stent is located at a proximal portion of the elongate body.

5. The system of claim 1, wherein a longitudinal cross-sectional profile of the axially inward wall of the retention member of the inner stent substantially matches a longitudinal cross-sectional profile of the axially outward wall of the retention member of the outer stent.

6. The system of claim 1, wherein the axially outward wall of the retention member of the inner stent extends to a flexible sleeve contiguous with the lumen of the outer stent.

7. The system of claim 1, wherein a diameter of the cylindrical saddle region of the inner stent is different than a diameter of the cylindrical saddle region of the outer stent.

8. The system of claim 1, wherein the radial wall of the outer stent comprises a diameter greater than a diameter of the cylindrical saddle region of the outer stent.

9. The system of claim 1, wherein the elongate body of the outer stent comprises a braid and wherein the cylindrical saddle region of the outer stent is twisted to a reduced diameter portion.

10. The system of claim 1, wherein the radial wall of the outer stent comprises a diameter greater than a diameter of the radial wall of the inner stent.

11. The system of claim 1 further comprising a covering extending at least partially along a length of the elongate body of the outer stent.

12. The system of claim 1, further comprising a radiopaque marker at each of the retention member of the inner stent and the retention member of the outer stent.

13. The system of claim 1, wherein the inner stent further comprises an element configured for reducing a profile of the inner stent and removing the inner stent from the outer stent.

14. The system of claim 1, further comprising a flexible sleeve coupled to the inner stent and extending axially away from the retention member of the outer stent.

* * * * *